United States Patent
Libbus et al.

(10) Patent No.: US 11,786,732 B2
(45) Date of Patent: *Oct. 17, 2023

(54) R-R INTERVAL ANALYSIS FOR ECG WAVEFORMS TO ASSESS AUTONOMIC RESPONSE TO VAGUS NERVE STIMULATION

(71) Applicant: LivaNova USA, Inc., Houston, TX (US)

(72) Inventors: Imad Libbus, St. Paul, MN (US); Scott R. Stubbs, Maple Grove, MN (US); Scott Mazar, Woodbury, MN (US); Bruce KenKnight, Maple Grove, MN (US); Badri Amurthur, Los Gatos, CA (US)

(73) Assignee: LivaNova USA, Inc., Houston, TX (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/054,982

(22) PCT Filed: May 13, 2019

(86) PCT No.: PCT/US2019/031997
§ 371 (c)(1),
(2) Date: Nov. 12, 2020

(87) PCT Pub. No.: WO2019/222089
PCT Pub. Date: Nov. 21, 2019

(65) Prior Publication Data
US 2021/0268286 A1  Sep. 2, 2021

Related U.S. Application Data

(60) Provisional application No. 62/671,986, filed on May 15, 2018.

(51) Int. Cl.
*A61N 1/36* (2006.01)

(52) U.S. Cl.
CPC ...... *A61N 1/36114* (2013.01); *A61N 1/36139* (2013.01)

(58) Field of Classification Search
CPC ................. A61N 1/36114; A61N 1/36139
(Continued)

(56) References Cited

U.S. PATENT DOCUMENTS

| 7,103,414 B1 | 9/2006 | Poore et al. |
| 8,239,028 B2 | 8/2012 | Scott |

(Continued)

FOREIGN PATENT DOCUMENTS

| CN | 105009315 A | 10/2015 |
| WO | WO-2007/115118 A1 | 10/2007 |
| WO | WO-2013/086163 A1 | 6/2013 |

OTHER PUBLICATIONS

International Search Report and Written Opinion on PCT/US2019/031997 dated Jul. 26, 2019. 10 pages.
(Continued)

*Primary Examiner* — Alyssa M Alter
(74) *Attorney, Agent, or Firm* — Foley & Lardner LLP

(57) ABSTRACT

An assessment system is provided for vagus nerve stimulation treatment with a neurostimulator configured to deliver a stimulation signal having a plurality of ON-periods and OFF-periods. The assessment system includes a wand assembly configured to generate a delivery detection signal indicating delivery of the stimulation signal, a lead assembly configured to acquire an ECG signal, and a data acquisition system configured to capture the delivery detection and ECG signals. The assessment system further includes a processor and a non-transitory computer-readable memory storing instructions that, when executed by the processor, cause the (Continued)

assessment system to record the ECG signal over at least one successive pair of ON- and OFF-periods, determine a heart rate dynamic response from the ECG signal, and determine an instantaneous heart rate for each determined R-R interval to determine heart rate dynamics for assessment of autonomic engagement in response to the vagus nerve stimulation treatment.

29 Claims, 14 Drawing Sheets

(58) Field of Classification Search
USPC .......................................................... 607/59
See application file for complete search history.

(56) References Cited

U.S. PATENT DOCUMENTS

| | | | |
|---|---|---|---|
| 9,079,034 B2 | 7/2015 | Milbocker | |
| 2003/0040774 A1 | 2/2003 | Terry et al. | |
| 2005/0182755 A1 | 8/2005 | Tran | |
| 2006/0241725 A1 | 10/2006 | Libbus et al. | |
| 2007/0027496 A1 | 2/2007 | Parnis et al. | |
| 2007/0255330 A1 | 11/2007 | Lee et al. | |
| 2008/0118126 A1 | 5/2008 | Sakaguchi | |
| 2008/0140141 A1* | 6/2008 | Ben-David | A61N 1/36114 607/9 |
| 2010/0191304 A1 | 7/2010 | Scott | |
| 2010/0274308 A1 | 10/2010 | Scott | |
| 2012/0083700 A1 | 4/2012 | Osorio | |
| 2012/0185007 A1 | 7/2012 | Ziegler et al. | |
| 2013/0158618 A1 | 6/2013 | Libbus et al. | |
| 2013/0253616 A1 | 9/2013 | Libbus et al. | |
| 2014/0364921 A1 | 12/2014 | Legay et al. | |
| 2015/0073237 A1 | 3/2015 | Osorio | |
| 2015/0306395 A1 | 10/2015 | Libbus et al. | |
| 2015/0374983 A1 | 12/2015 | Simon et al. | |
| 2016/0038754 A1 | 2/2016 | Adjouadi et al. | |
| 2016/0101289 A1 | 4/2016 | Stolen et al. | |
| 2016/0158554 A1* | 6/2016 | Graig | A61N 1/36064 607/62 |
| 2016/0339242 A1 | 11/2016 | Cook et al. | |
| 2019/0247664 A1 | 8/2019 | Irazoqui et al. | |
| 2020/0345251 A1 | 11/2020 | Falk et al. | |

OTHER PUBLICATIONS

EP Search Report on EP Appl. Ser. No. 19803063.7 dated Jan. 28, 2022 (10 pages).

Libbus et al., "Quantitative evaluation of heartbeat interval time series using Poincare analysis reveals distinct patterns of heart rate dynamics during cycles of vagus nerve stimulation in patients with heart failure," Journal of Electrocardiology, Jun. 8, 2017, vol. 50, No. 6 (pp. 898-903) p. 900, left-hand column; figure 2*.

CN First Office Action for CN Appl. Ser. No. 201980003312.9 dated Jun. 10, 2020 (11 pages).

CN Second Office Action on CN Appl. Ser No. 201980003312.9 dated Dec. 30, 2020 (8 pages).

EP Office Action on EP Appl. Ser. No. 19802790.6 dated Feb. 17, 2022 (1 page).

EP Search Report on EP Appl. Ser. No. 19802790.6 dated Jan. 31, 2022 (10 pages).

EP Search Report on EP Appl. Ser. No. 19803136.1 dated Jan. 31, 2022 (5 pages).

EP Supplementary Search Report on EP Appl. Ser. No. 19803728.5 dated Jan. 25, 2022 (10 pages).

International Search Report and Written Opinion for PCT Appl. Ser. No. PCT/US2019/031992 dated Jul. 22, 2019. (9 pages).

International Search Report and Written Opinion on PCT Appl. Ser. No. PCT/US2019/031991 dated Jul. 29, 2019 (10 pages).

International Search Report and Written opinion on PCT Appl. Ser. No. PCT/US2019/031994 dated Jul. 24, 2019 (9 pages).

* cited by examiner

R-R INTERVAL ANALYSIS FOR ECG WAVEFORMS TO ASSESS AUTONOMIC RESPONSE TO VAGUS NERVE STIMULATION

CROSS-REFERENCE TO RELATED PATENT APPLICATION

This application is a U.S. National Stage Application of PCT/US2019/031997, filed May 13, 2019, which claims the benefit of and priority to U.S. Provisional Patent Application No. 62/671,986, entitled "SYSTEMS AND METHODS FOR R-R INTERVAL ANALYSIS IN ECG WAVEFORMS TO ASSESS AUTONOMIC RESPONSE TO VAGUS NERVE STIMULATION THERAPY IN TREATMENT OF CONGESTIVE HEART FAILURE," filed May 15, 2018, which is incorporated herein by reference in its entirety.

TECHNICAL FIELD

The present disclosure relates generally to systems and methods of neurostimulation therapy and, in particular, to systems and methods for assessing autonomic response to vagus nerve stimulation therapy in the treatment of congestive heart failure.

BACKGROUND

Autonomic regulation neurostimulation therapy delivered by vagus nerve stimulation ("VNS") is a treatment for congestive heart failure. VNS therapy commonly requires implantation of a neurostimulator, which, when activated, applies or delivers a stimulation signal to the vagus nerve of a patient. A vagus nerve stimulation signal is typically a periodic current pulse signal defined by an output current amplitude or intensity. Following implantation and activation of the neurostimulator, a full therapeutic dose of VNS is not immediately delivered to the patient to avoid causing significant patient discomfort and other undesirable side effects. Instead, to allow the patient to adjust to the VNS therapy, a titration process is utilized in which the intensity is gradually increased over a period of time under the control of a physician with the patient given time between successive increases in VNS therapy intensity to adapt to the new intensity. As stimulation is chronically applied at each new intensity level, the patient's side effect threshold gradually increases, allowing for an increase in intensity during subsequent titration sessions.

SUMMARY

Embodiments of systems and methods are provided for monitoring physiological response to vagus nerve neurostimulation therapy. One embodiment relates to an assessment system for vagus nerve stimulation therapy treatment for congestive heart failure in a subject implanted with a neurostimulator configured to deliver a periodic stimulation signal having a plurality of ON-periods and OFF-periods. Each ON-period is defined as time between an initiating pulse and a terminating pulse of a plurality of stimulation pulses delivered to the subject, and each OFF-period is defined as a time between consecutive ON-periods. The assessment system includes a wand assembly in communication with the neurostimulator and configured to generate a delivery detection signal indicating delivery of the stimulation signal, a lead assembly configured to acquire an ECG signal of the subject over the plurality of ON-periods and OFF-periods, and a data acquisition system coupled to the wand and lead assemblies and configured to capture each of the delivery detection signal and the ECG signal. The assessment system further includes a processor and a non-transitory computer-readable memory storing instructions that, when executed by the processor, cause the assessment system to record the ECG signal over at least one successive pair of ON- and OFF-periods including, for each pair of ON- and OFF-periods, synchronizing a start of the recorded ECG signal to provide a first portion of the recorded ECG signal corresponding to the ON-period and a second portion of the recorded ECG signal corresponding to the OFF-period. The instructions also cause the assessment system to determine a heart rate dynamic response from the ECG signal, including detecting each QRS complex in each of the first and second portions of the recorded digital ECG signal, identifying each potential R-wave in each QRS complex in each of the first and second portions of the recorded ECG signal, verifying each identified R-wave in each of the first and second portions of the recorded ECG signal, and determining an R-R interval between each pair of successive verified R-waves. The instructions further cause the assessment system to determine an instantaneous heart rate for each determined R-R interval to determine heart rate dynamics for assessment of autonomic engagement in response to the vagus nerve stimulation treatment.

Another embodiment relates to an assessment system for vagus nerve stimulation therapy treatment for congestive heart failure in a subject. The assessment system includes a lead assembly configured to acquire an analog ECG signal of the subject over a delivery period of vagus nerve stimulation delivered to the subject and defined by an initiating pulse and a terminating pulse, the delivery period being a time between the initiating and terminating pulses, a data acquisition system coupled to the lead assembly and configured to convert the analog ECG signal to a digital ECG signal over the delivery period, and a processor and a non-transitory computer-readable memory. The memory stores instructions that, when executed by the processor, cause the assessment system to detect each QRS complex in the digital ECG signal over the delivery period, identify each potential R-wave in each QRS complex of the digital ECG signal, confirm each R-wave of the digital ECG signal, determine a time interval between each pair of successive confirmed R-waves of the digital ECG signal, and determine an instantaneous heart rate from each determined time interval.

Another embodiment relates to a method of real-time assessment of autonomic engagement response to vagus nerve stimulation therapy. The method includes determining, in real-time, R-R intervals in an ECG signal response to a stimulation cycle of the therapy, the stimulation cycle having an ON-period during which therapy is delivered and an OFF-period during which therapy is not delivered. The method further includes distinguishing the R-R intervals occurring during the ON-period from the R-R intervals occurring during the OFF-period to assess the autonomic engagement response to the stimulation cycle.

BRIEF DESCRIPTION OF THE DRAWINGS

The accompanying drawings, which are incorporated herein and constitute part of this specification, illustrate exemplary embodiments of the systems and methods described herein, and together, with the general description given above and the detailed description given below, serve to explain the features of the invention.

DETAILED DESCRIPTION

When delivering neurostimulation therapies to patients, it is generally desirable to avoid stimulation intensities that result in either excessive tachycardia or excessive bradycardia side effects. The neurostimulator may be adjusted to deliver varying stimulation intensities to the patient. To find a beneficial therapeutic level of neurostimulation, researchers have utilized the patient's heart rate changes. Some researchers have proposed that heart rate reduction serves as a functional response indicator or surrogate for effective recruitment of nerve fibers and engagement of the autonomic nervous system elements, which may be indicative of therapeutic levels of vagus nerve stimulation. A therapeutic level or dose of vagus nerve stimulation that results in a heart rate reduction of up to 5% has been described as treatment that is delivered within the desired "neural fulcrum zone." The neural fulcrum zone corresponds to a combination of stimulation parameters at which autonomic engagement is achieved but for which a functional response determined by heart rate change is nullified due to the competing effects of afferently and efferently-transmitted action potentials. In this way, the tachycardia-inducing stimulation effects are offset by the bradycardia-inducing effects, thereby minimizing side effects, such as significant heart rate changes, while providing a therapeutic level of stimulation.

Figure 1:
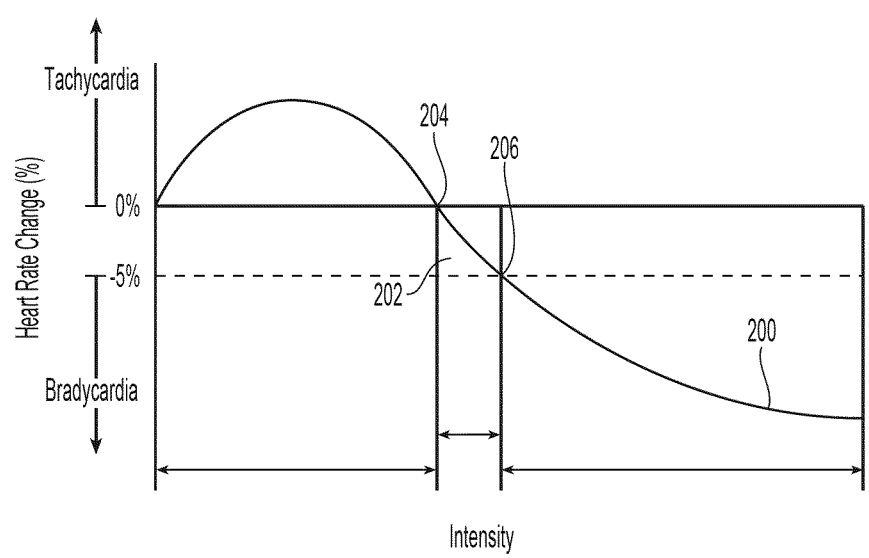
FIG. 1 is an illustrative graphic of a heart rate change response as a function of stimulation signal intensity, according to an exemplary embodiment.

Shown in FIG. 1 is a graphic illustration of the neural fulcrum zone and heart rate change response as a function of increasing vagus nerve stimulation signal intensity and constant frequency. The x-axis represents the intensity level of the stimulation signal, and the y-axis represents the observed heart rate change from the patient's baseline basal heart rate observed when no stimulation is delivered. The patient's heart rate change response 200 is depicted as depending on the stimulation signal intensity. As the intensity (e.g., output current amplitude) is increased, a tachycardia zone is observed. This response 200 is more or less pronounced depending on the other stimulation parameters. As the intensity continues to be increased, the patient's heart rate change response 200 begins to decrease and eventually enters a bradycardia zone. The neural fulcrum zone is depicted as the response zone 202 between no heart rate change 0% (occurring at point 204) and a heart rate reduction of 5% (occurring at point 206).

In vagus nerve stimulation therapy, the titration process can take up to 10-12 weeks before a full therapeutic dosage can even be tolerated. In order to reduce or minimize the titration process time to a full therapeutic dose, it is desirable to monitor the physiological response to evaluate whether the applied stimulus dosage in the titration process is effective without inducing undesirable side effects. Accordingly, there remains a need for systems and methods to assess autonomic engagement response to delivery of a vagus nerve stimulation signal.

Figure 2:
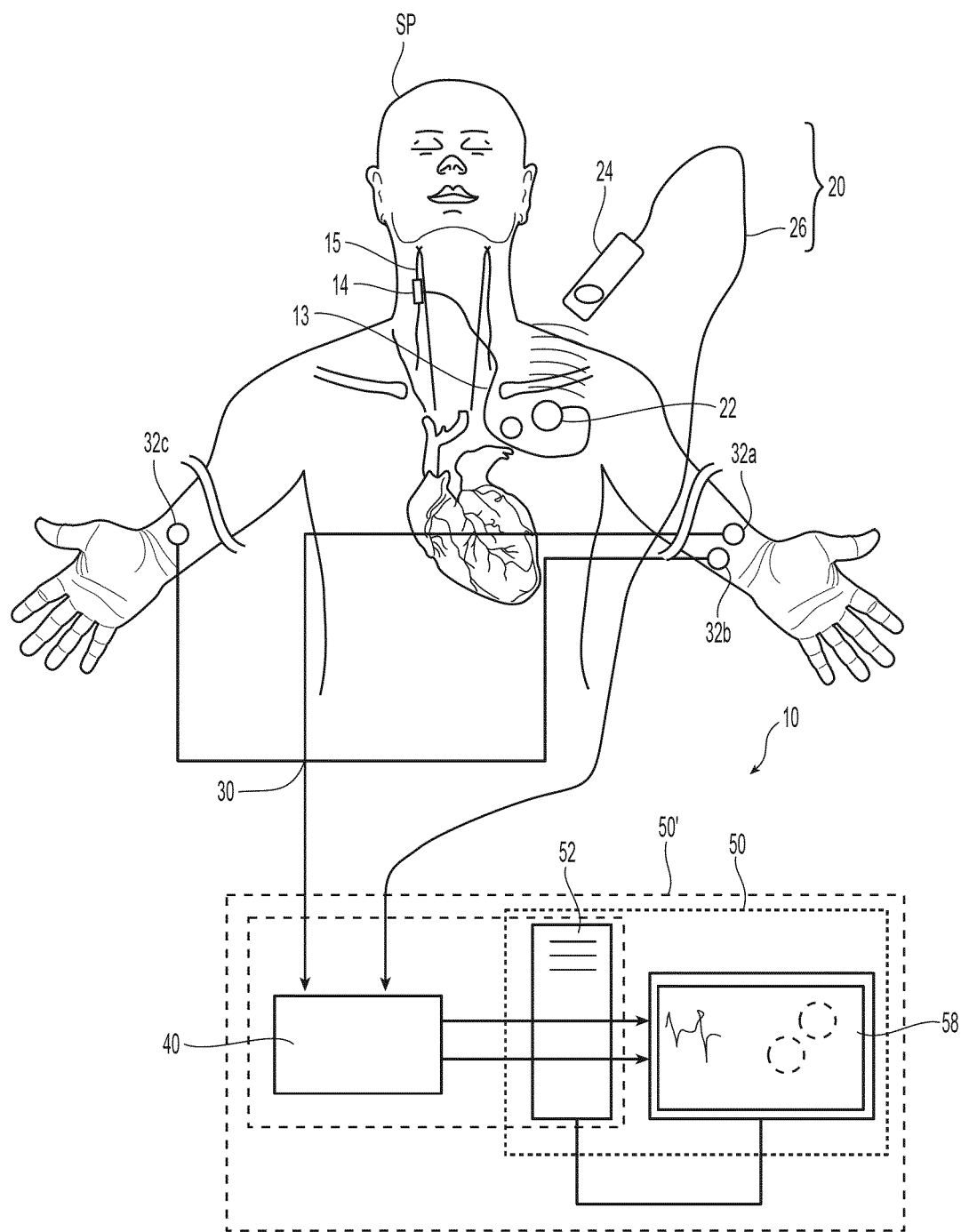
FIG. 2 a schematic view of a system for assessing vagus nerve stimulation from an implanted neurostimulator for treatment of congestive heart failure ("CHF"), according to an exemplary embodiment.

Shown in FIG. 2 is a system 10 for monitoring and assessing a physiological response of a subject patient SP to neurostimulation therapy and, in particular, for monitoring and assessing heart rate dynamic response to vagus nerve stimulation for the treatment of CHF, according to an exemplary embodiment. In various embodiments, the system 10 provides one or more indicators to a patient and/or clinician of the effectiveness of a delivered stimulation treatment by indicating autonomic engagement in the subject patient SP in a timeframe that is real-time, which includes a timeframe that is instantaneous, immediate, sequential, or proximate to a parameter change; encompassing a titration session; and/or within one minute, ten minutes, and/or an hour of a stimulation parameter change. In some embodiments, the one or more real-time indicators of the effectiveness of a delivered stimulation treatment allow and/or facilitate the modification of the stimulation therapy, the subject patient SP's advancement through the titration process, and/or the delivery of effective levels of therapy to the subject patient SP in a timeframe that is real-time, which includes a timeframe that is instantaneous, immediate, sequential, or proximate to a parameter change; encompassing a titration session; and/or within one minute, ten minutes, and/or an hour of a stimulation parameter change. Alternatively or additionally, the titration process can be automatically altered or increased in intensity with the detection, monitoring, and/or measurement by the system 10 occurring in real-time. The assessment can be read from system 10 in real-time, or, if needed or desired, the assessment can be read from the system 10 by a clinician at a later time in a clinic or other environment.

The system 10 captures the physiological response to the vagus nerve stimulation. In some embodiments, the system 10 (i) detects the electrical heart activity response, e.g., electrocardiogram ("ECG") of the subject patient SP in response to the vagus nerve stimulation; (ii) determines the change in heart rate dynamics in response to the stimulation; and (iii) visually displays the change in heart rate dynamics in a manner that indicates the extent of autonomic engagement in response to the delivered stimulus. By providing the indication of autonomic engagement in real-time, the effectiveness of the stimulus treatment can be assessed by the patient or clinician, and the stimulus can be adjusted as needed in real-time to ensure delivery of an effective stimulus or the delivery of a stimulus that advances the titration of the subject patient SP to an effective stimulus. Moreover, by assessing a stimulation signal of a titration process in real-time, the stimulation signal can be optimized and the overall titration process and the therapy can be made more efficient by minimizing the time required to achieve a titrated delivery of a full therapeutic dose or intensity of a vagus nerve stimulus.

The system 10 includes a first interface or communication assembly 20 for communication with a stimulation delivery device 22 and a second interface assembly 30 for capturing the physiological response of the subject patient SP. In some embodiments, the second interface assembly 30 captures data suitable for generating the ECG waveform of the subject patient SP to the stimulation delivery. In various embodiments, as shown in FIG. 2, the stimulation delivery device 22 is embodied as an implantable medical device ("IMD") and, more particularly, an implantable neurostimulator 22. Embodiments of the neurostimulator 22 are shown and described in U.S. Pat. Nos. 9,770,599 and 9,950,169, each of which is incorporated by reference in its entirety. As described in the cited patent documents, the implantable medical device includes a pulse generator 22, a lead 13, and electrodes 14 for delivering a pulse generated stimulus about a vagus nerve 15 of the subject patient SP. A commercially available embodiment of the implantable neurostimulator 22 includes the VITARIA™ Model 7103 Pulse Generator from Livallova USA, Inc. of Houston, Tex., USA.

Figure 3:
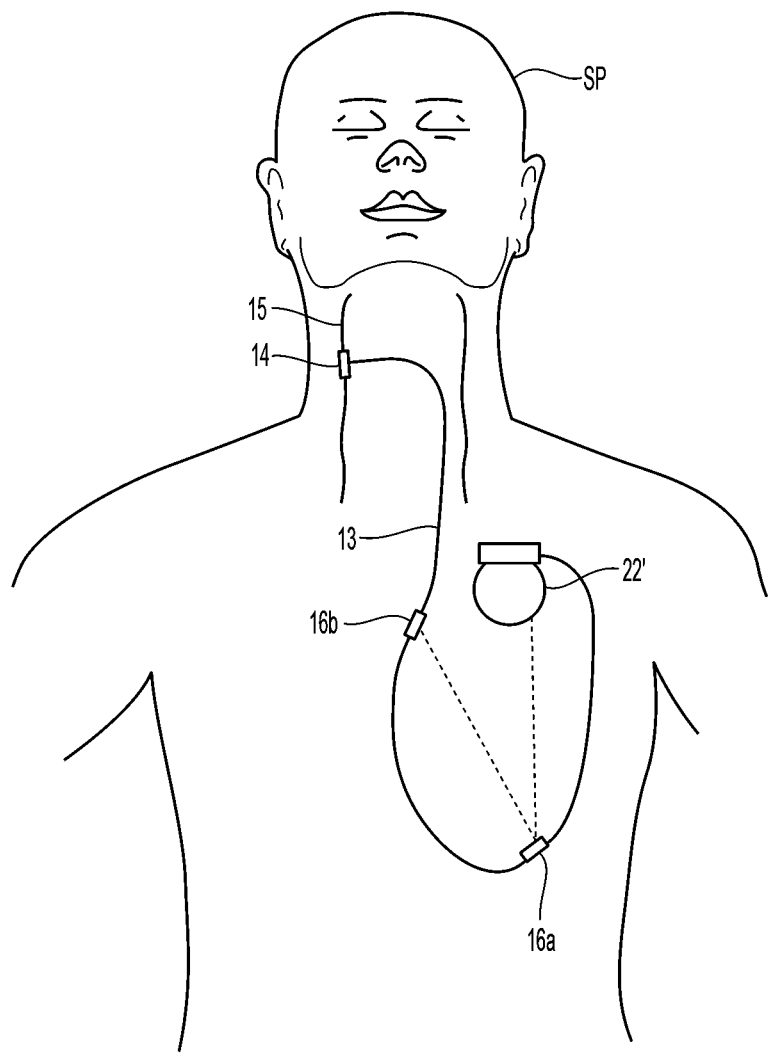
FIG. 3 is another schematic view of a neurostimulator for use in the system of FIG. 2, according to an exemplary embodiment.

Shown in FIG. 3 is another embodiment of a neurostimulator 22', for use with the assessment system 10, which includes or incorporates an implantable cardioverter-defibrillator ("ICD"). An implantable VNS/ICD system is also shown and described in U.S. Pat. No. 9,770,599, which is incorporated by reference in its entirety. An embodiment of an implantable VNS/ICD system includes a pulse generation module with a control system, a VNS subsystem, and an ICD subsystem. A first electrode assembly 14 is coupled to the pulse generation module and includes a VNS electrode configured to couple to the vagus nerve 15. A second electrode assembly 16a, 16b is coupled to the pulse generation module and includes a subcutaneous electrode. Another embodiment of an implantable VNS/ICD system includes a primary pulse generation module having a primary control system and an ICD subsystem and a secondary pulse generation module having a secondary control system and a VNS subsystem. The secondary pulse generation module is placed in data communication with the primary pulse generation module, with the second electrode assembly 16a, 16b coupled to the primary pulse generation module, in which the second electrode assembly 16a, 16b includes a subcutaneous electrode. Another electrode assembly is coupled to the secondary pulse generation module. This electrode assembly includes a VNS electrode 14 configured to couple to the vagus nerve 15. In various embodiments, the implantable VNS/ICD system is configured to deliver a chronic VNS therapy to the vagus nerve 15 with a VNS subsystem of a pulse generation module. In response to detection of a cardiac event, the implantable VNS/ICD system is configured to deliver electrical cardioversion-defibrillation energy with an ICD subsystem of the pulse generation module.

Referring back to FIG. 2, a computer processing device 50 is coupled with the first and second interfaces 20, 30 for processing the captured ECG-suitable signal to determine, for example, in real-time, the heart rate dynamics in the subject patient SP in response to delivery of the stimulation signal to the vagus nerve 15. The ECG-suitable signal allows the determination and display of a periodic waveform with repeating "cardiac cycles" as shown, for example, in FIG. 13. A "cardiac cycle" may refer to one complete PQRSTU interval of the patient's heart functioning, ending with the P wave of the next succeeding cardiac cycle. An "interbeat interval" may refer to the time period between a predetermined point in a first cardiac cycle of the patient and the same predetermined point in the immediately succeeding cardiac cycle of the patient. Examples of interbeat intervals include an R-R interval, a P-P interval, or a T-T interval. Interbeat intervals may include a single interval or a moving average (either simple or weighted) of several consecutive intervals. Within a single cardiac cycle, a "cardiac period" is a length of time between a first point in the cardiac cycle of the patient and a second, later point. An exemplary cardiac period includes a P-wave, a Q-wave, an R-wave, an S-wave, a QRS complex, a T-wave, and a U-wave of the cardiac cycle, which can be readily identified by electrocardiography or other techniques of monitoring the electrical activity of the heart. For example, the R-wave presents the maximum amplitude of the cardiac cycle.

According to one embodiment of the processing of the ECG-suitable signal described herein, the heart rate dynamics are determined from an R-R interbeat interval analysis of the cardiac period QRS complex in the ECG waveform. From the heart rate dynamics, the computer processing device 50 displays in real-time an indication of autonomic engagement in the subject in response to the stimulus. The R-R interval analysis provides a desired resolution in the ECG waveform from which to determine and indicate the autonomic response in real-time.

Figure 4:
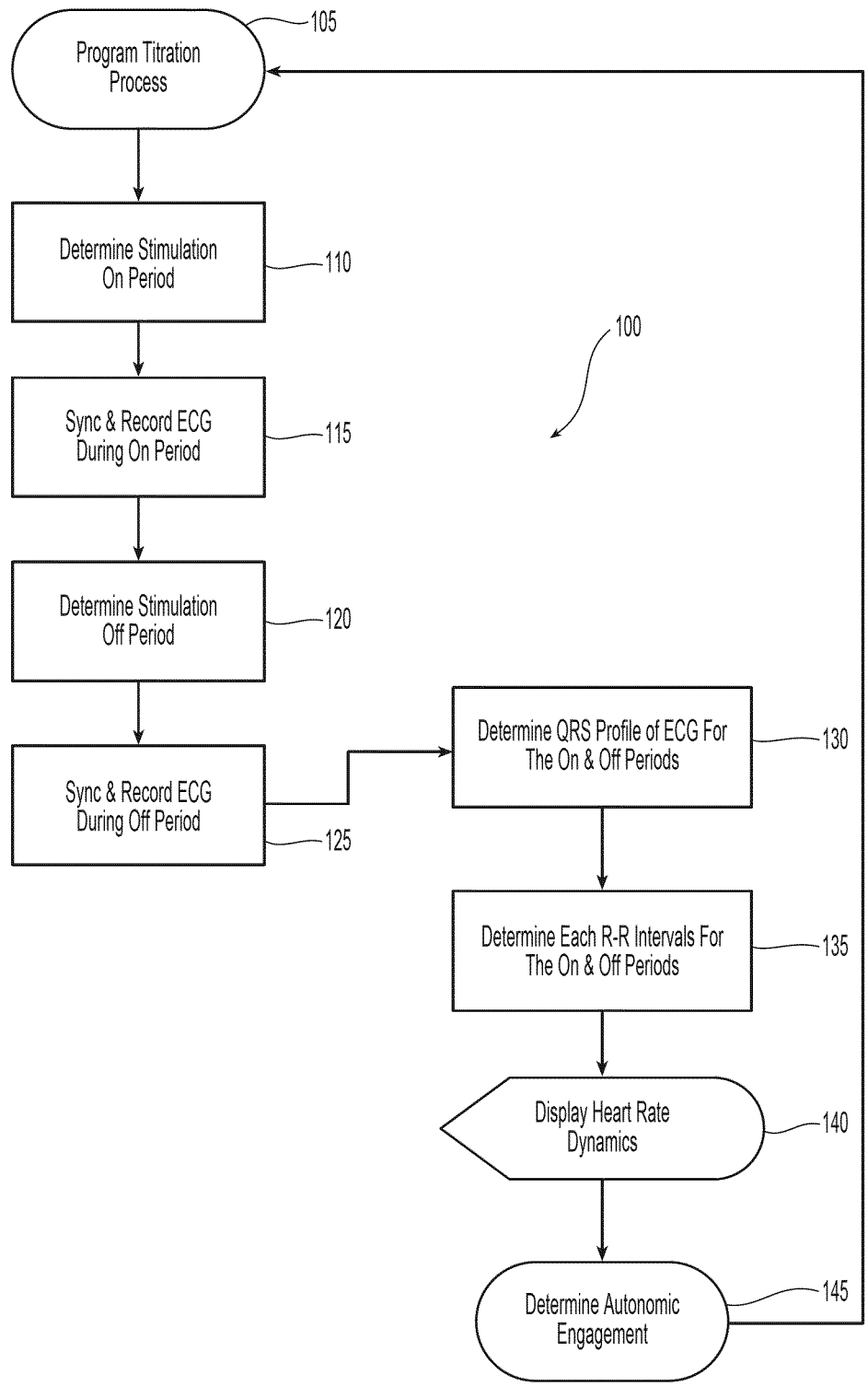
FIG. 4 is a flow chart of a method of assessment, according to an exemplary embodiment.

Shown in FIG. 4 is a process 100 for capturing and analyzing the ECG-suitable signal response during vagus nerve stimulation treatment, according to an exemplary embodiment. At the beginning 105 of the titration or stimulation delivery process (e.g., as part of programming the titration process), a first determination step 110 is taken to determine when a stimulus signal is to be delivered from the neurostimulator 22 to the vagus nerve. In some embodiments, the stimulation signal is periodic having an ON-period in which stimulation of a particular current amplitude and frequency is delivered and an OFF-period of rest in which no stimulation signal is delivered to the vagus nerve. With the schedule of ON-periods determined, the process 100 includes a synchronization and recordation step 115 in which an ECG-suitable signal is captured and recorded over the ON-period. In a second determination step 120, the OFF-period of the stimulation signal is identified. In some embodiments, the OFF-period is continuous with the ON-period and is identifiable as being the rest period between two adjacent ON-periods in the stimulation signal. With the OFF-period identified, a second synchronization and recordation step 125 is carried out to capture and record the ECG-suitable signal over the OFF-period. Although FIG. 4 shows the determination and recordation steps as discrete steps, the steps may be carried out sequentially, concurrently, or in an alternate order.

Having captured and identified the ECG-suitable signals corresponding to each of the ON-period and OFF-period in the stimulation signal, a third determination step 130 is carried out to determine the QRS complex profile in the corresponding ECG waveforms for each period of the stimulation signal. A fourth determination step 135 includes determining each R-R interval between consecutive QRS complexes in each ECG-suitable signal corresponding to the ON-period and OFF-period in the stimulation signal. Accordingly, heart rate dynamic response, such as, for example, instantaneous heart rate, mean heart rate, and heart rate variability, can be determined and displayed in a subsequent step 140 for each of the ON-period and OFF-period in the stimulation signal. The process 100 can then conclude with an assessment step 145 in which the autonomic engagement response can be determined, indicated, and displayed for the subject patient and/or clinician.

Figure 5:
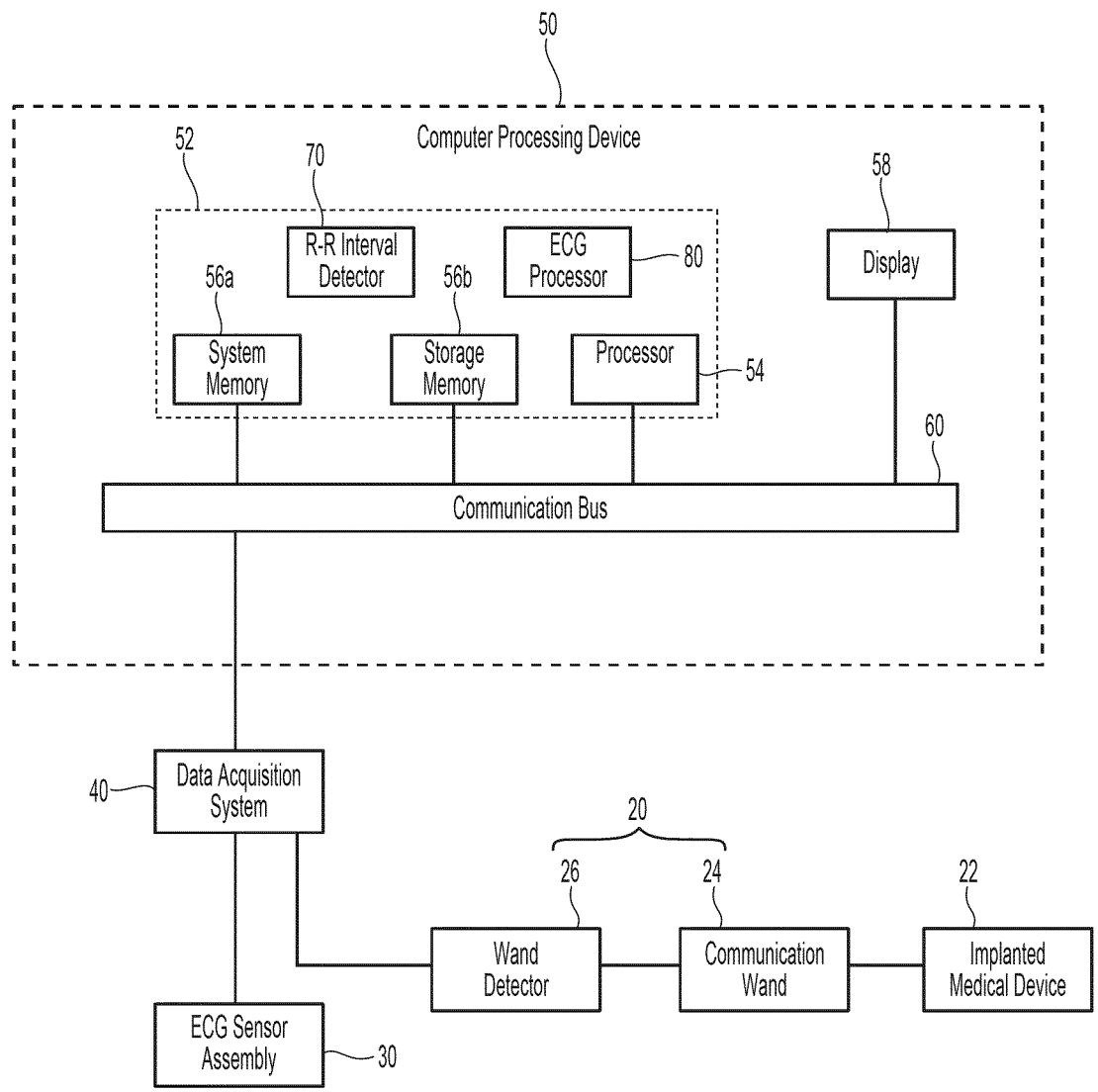
FIG. 5 is a schematic view of components of the system of FIG. 2, according to an exemplary embodiment.

Shown in FIG. 5 is another schematic view of the system 10 with the computer processing device 50 for assessing a vagus nerve stimulation treatment, according to an exemplary embodiment. The computer processing device 50 includes processing hardware 52, such as, for example, a central processing unit 54 and associated memory or computer readable medium, such as, for example, system memory 56a and storage memory 56b, for processing ECG-suitable signals in a manner as described herein. The system memory 56a can include volatile memory, such as, for example, RAM (random-access memory). The storage memory 56b can be non-volatile or persistent memory such as, for example, ROM (read-only memory), flash memory, ferroelectric RAM, most types of magnetic computer storage devices (e.g. hard disk drives, solid state drives, floppy disks, and magnetic tape), or optical discs. The computer processing device 50 includes one or more associated displays 58 for indicating the autonomic engagement response to the stimulus. The system memory 56a and/or storage memory 56b may store instructions that are executable by the processor 54 to perform the functionalities described herein. The display 56 can be a touch-sensitive display, which can provide touch control buttons and keys. As shown, the processing hardware 52 and the display 58 communicate with one another over a communication bus or network 60. Additionally or alternatively, the computer processing device 50 can include one or more peripheral input and output ports for connection and use with other peripheral input, output, or storage devices. The components of the computer processing device 50 can be integrated with one another or be separately housed components. For example, the processing hardware 52 can be housed separately from the display 58. Alternatively, the display 58 can be housed with the processing hardware 52 in a single assembly. In some embodiments, the computer processing device 50 can be embodied using a general purpose programmable computer. A general purpose programmable computer can be a personal computer, laptop computer, Ultrabook computer, netbook computer, handheld computer, tablet computer, smart phone, or other form of computational device with an appropriate operating system. In other embodiments, the computer processing device 50 can be a specialized computer specifically designed and programmed to function with the neurostimulator 22 described herein.

Referring back to FIG. 2, in the system 10, the computer processing device 50 is coupled to each of the first and second interface communication assemblies 20, 30 by a data acquisition system 40. The data acquisition system 40 provides for digital conversion of incoming signals coming from the interface communication assemblies 20, 30 (e.g., a wand assembly 20, ECG sensor assembly 30). The data acquisition system 40, the processing hardware 52, and the display 58 communicate with one another over a communication bus or network 60 (e.g., as shown in FIG. 5). In some embodiments, the data acquisition system 40 for use in the system 10 is the BIOPAC MP36R from BIOPAC® Systems, Inc., which can simultaneously capture signals from multiple devices or sources. Additionally, in some embodiments, the computer processing device and the data acquisition system are different systems (e.g., shown as computer processing device 50 and data acquisition system 40 in FIG. 2), while in other embodiments, the computer processing device and data acquisition system are incorporated into a single system (e.g., shown as computer processing device 50' in FIG. 2).

In the system 10, the communication assembly 20 wirelessly communicates with the neurostimulator 22 by providing control signals or commands to define parameters of the stimulation signal or pulses to be delivered by the neurostimulator 22 to the vagus nerve. In some embodiments, as shown in FIG. 2, the communication assembly 20 includes an external programming wand 24 and a wand transmission detection cable 26. The programming wand 24 wirelessly communicates with the implanted device 22 by telemetry or radio frequency signal. Embodiments of the external programming wand 24 are described, for example, in U.S. Pat. Nos. 9,770,599 and 9,950,169. A commercially available embodiment of the wand 24 includes NeuroCybernetic Prosthesis (NCP®) Programming Wand Model 201. The wand 24 is a hand-held device that can transmit programming and interrogation information signals or commands to the implantable neurostimulator 22, such as, for example, the VITARIA™ Model 7103 Pulse Generator. The programming wand 24 alone or in conjunction with a computer and appropriate firmware, such as, for example VNS Therapy Programming Software, can store and retrieve telemetry data and revise stimulus signal parameters from the pulse generator 22.

The wand transmission detection cable 26 is associated with the external programmer or wand 24 to detect or determine the stimulation delivery from the neurostimulator 22 to the vagus nerve 15 of the subject patient SP. In some embodiments, the wand transmission detection cable 26 detects or extracts the delivery schedule from the external wand 24 to determine the stimulation delivery from the neurostimulator 22 to the vagus nerve 15. By detecting delivery of stimulation signals with the communication assembly 20, the capture or recording of the subject's ECG-suitable signal can be synchronized with the ON-period and OFF-period of the stimulation signal in accordance with the process 100 for capturing and analyzing the ECG-suitable signal previously described.

In some implementations, the second interface assembly 30 is embodied as an ECG cable assembly with three leads or clips 32a, 32b, 32c for respectively connecting to three electrodes or contacts, for example, placed on the wrists of the subject patient SP. As seen in FIG. 2, two leads 32a, 32b are connected to two electrodes on the left wrist and the remaining lead 32c is connected to a single electrode on the patient's right wrist.

The computer processing device 50 operates under the control of one or more software applications, which are executed as program code as a series of process or method modules or steps by the programmed computer hardware. In some embodiments, a computer readable medium, such as a non-transitory computer readable medium, of the processing hardware 52 stores a program that can cause the computer processing device 50 to execute one or more processes described herein for assessing vagus nerve stimulation treatment.

In the embodiment of the system 10 and its operation 100 of FIG. 4, the system 10 processes the ECG-suitable signal response to determine the ECG waveform and the R-R intervals to derive heart rate dynamics in assessment of the stimulus treatment. Moreover, the system 10 distinguishes or identifies which portions of the ECG signal or waveform response correspond to the delivery of stimulation signal, i.e., the ON-periods of the periodic stimulation signal, and which portions of the ECG signal or waveform response correspond to the rest period, i.e., over the OFF-periods, of the periodic stimulation signal. By segregating ECG signals or portions of the ECG waveforms and their derivative components by ON-period and OFF-period, the ECG signals/waveforms and the heart rate dynamics derived therefrom can be compared to assess the extent of autonomic engagement resulting in the delivered stimulation signal.

Referring again to FIG. 5, the computer processing device 50 and its hardware includes and executes firmware programming that provides for an R-R interval detector 70 and an ECG processor 80 for carrying out the assessment methods described herein. The R-R interval detector 70 and ECG processor 80 and the associated methods can be implemented using appropriate software programming for signal processing and hardware configuration. For example, an appropriate "graphical program" can be used to represent data structures and/or program instructions in memory (e.g., the system memory 56*a* and/or storage memory 56*b*) of the computer processing device 50 to carry out the signal processing, instrument access, and assessment methods described herein. An exemplary graphical program development environment in which to create a program for use in the system 10 includes LabVIEW from National Instruments Corp.

Figure 6:
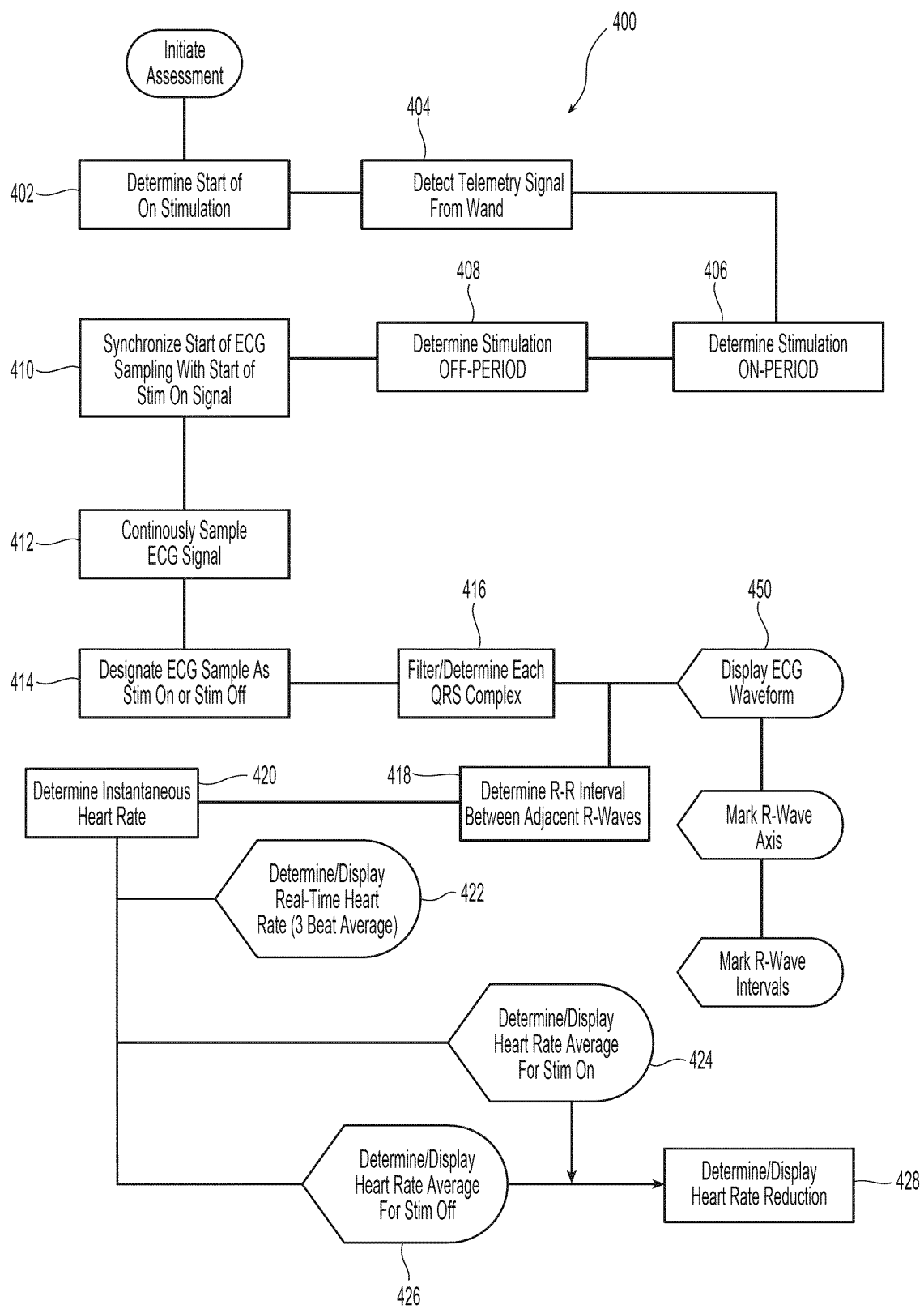
FIG. 6 is another embodiment of a method for assessing autonomic engagement response to vagus nerve stimulation therapy using the system of FIG. 2.

Shown in FIG. 6 is an embodiment of the assessment process 400. With the subject patient SP connected to the system 10, as shown in FIG. 2, and the implanted neurostimulator medical device 22 delivering a stimulation signal to the vagus nerve of the patient, the process of assessment 400 begins with a determination step 402 to determine the start of stimulation delivery for synchronizing recordation of the cardiac response. In some embodiments, the programming wand 24 is placed in communication with the neurostimulator 22, and the wand transmission detection cable 26 in combination with the computer processing device 50 detects the inductive telemetry signal between the components (step 404). The computer processing device 50 processes the inductive telemetry signals to determine the stimulation ON-period (step 406) and determine the stimulation OFF-period (step 408). Additionally, in some embodiments, the computer processing device 50 captures the various defining parameters of the delivered stimulation signal from which recordation of the ECG or other measure of cardiac response can be synchronized. At step 410, the computer processing device 50 synchronizes sampling of the ECG-suitable signal with the start of the ON-period of the delivered stimulation signal (e.g., such that, at step 412, the ECG-suitable signal is continuously recorded).

Figure 7:
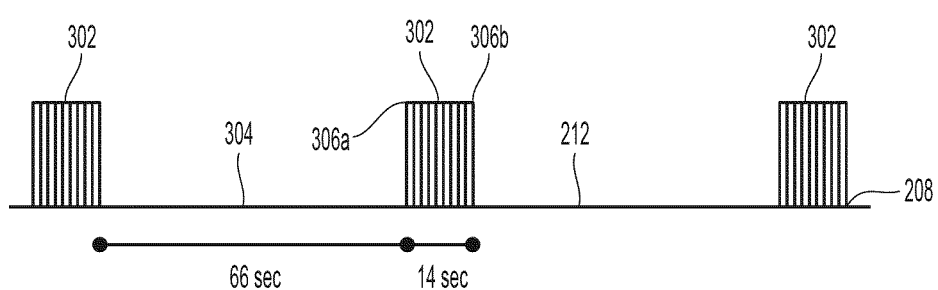
FIG. 7 is an illustrative schematic view of a stimulus signal, according to an exemplary embodiment.

Shown in FIG. 7 is an exemplary stimulus signal 300 defined by one or more of the following parameters: output current amplitude or intensity, signal frequency, or pulse width. The vagus stimulation signal 300 is delivered in a cyclical manner in which each cycle of is defined by an ON-period 302 in which the stimulation signal is delivered to the vagus nerve and an OFF-period or rest period 304 in which no stimulation is delivered. The ON-period 302 occurs at a constant interval with the OFF-periods 304 of rest between the repeating ON-periods 302. In some embodiments, a treatment cycle can be defined by a combination of on and off times selected from the following exemplary ON-periods: 7 sec, 14 sec, 21 sec, 30 sec, 50 sec, and 60 sec; and exemplary OFF-periods: 12 sec, 18 sec, 24 sec, 30 sec, 42 sec, 54 sec, 66 sec, 78 sec, 90 sec, 120 sec, 180 sec, and 300 sec. For example, one exemplary treatment cycle is defined by a 14 second "on period" and a 66 second "off period."

Figure 8:
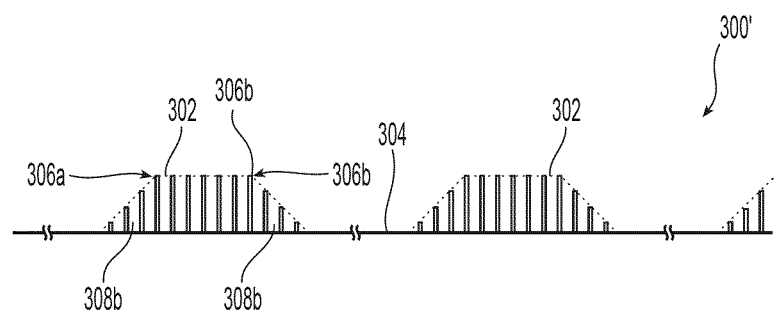
FIG. 8 is an illustrative schematic view of another stimulus signal, according to an exemplary embodiment.

As discussed above, a cycle of stimulation delivery is defined by a continuous ON-period and OFF-period. In some embodiments of treatment, there are 5-10 cycles. Each ON-period is defined by repeating pulse signals at a defined output current amplitude or intensity, signal frequency, and pulse width. In one exemplary ON-period, the pulse signals are defined by an output current of up to 3.0 mA, a frequency of 5-10 Hz, and a pulse width at 250-300 micro-seconds ("µsec"). Accordingly, each ON-period is defined by an initiating pulse 306*a* and a terminating pulse 306*b* that are spaced apart over a time duration defining the ON-period 302. The OFF-period 304 is thus defined by the time duration between a terminating pulse 306*b* of one ON-period 302 and the initiating pulse 306*a* of the consecutive, subsequent ON-period 302. Shown in FIG. 8 is another embodiment of a stimulation signal 300', which includes a ramp up period 308*a* to the initiating pulse 306*a* and a ramp down period 308*b* from the terminating pulse 306*b* (e.g., with the ramping up period 308*a* and the ramping down period 308*b* both being at a constant rate).

Referring again to FIG. 5 and FIG. 6, with the start of ECG signal recording synchronized with the stimulation signal, the ECG-suitable signal is continuously sampled at step 412 by the data acquisition system 40 and the computer processing device 50. For example, the ECG-suitable signal is sampled at a rate of 200 samples per second at a rate suitable for analysis and processing as described herein. In some embodiments, the ECG-suitable signal is recorded for at least one successive pair of ON- and OFF-periods. More particularly, in some embodiments, the ECG-suitable signal is recorded over a plurality of successive pairs of ON- and OFF-periods. In an exemplary ECG processing step 414, the digitally converted ECG-suitable signal is segregated and designated into portions that correspond to the ECG response to the ON-period of stimulation delivery and the ECG response to the resting OFF-period.

Figure 9:
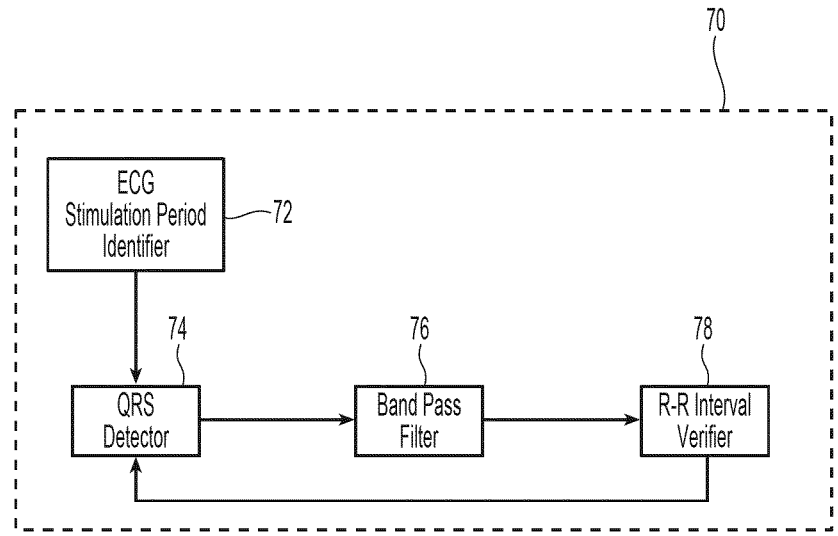
FIG. 9 is a schematic view of an embodiment of an R-R interval detector for use in the system of FIG. 2.
Figure 10:
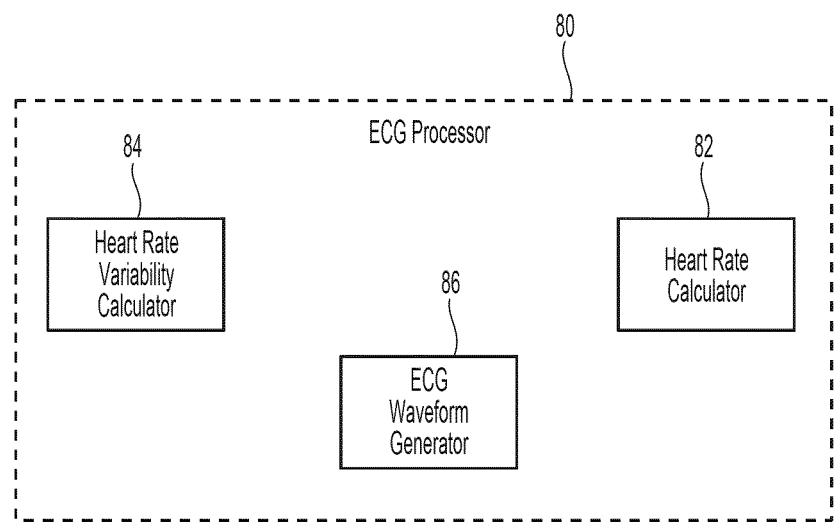
FIG. 10 a schematic view of an embodiment of an ECG processor for use in the system of FIG. 2.
Figure 11:
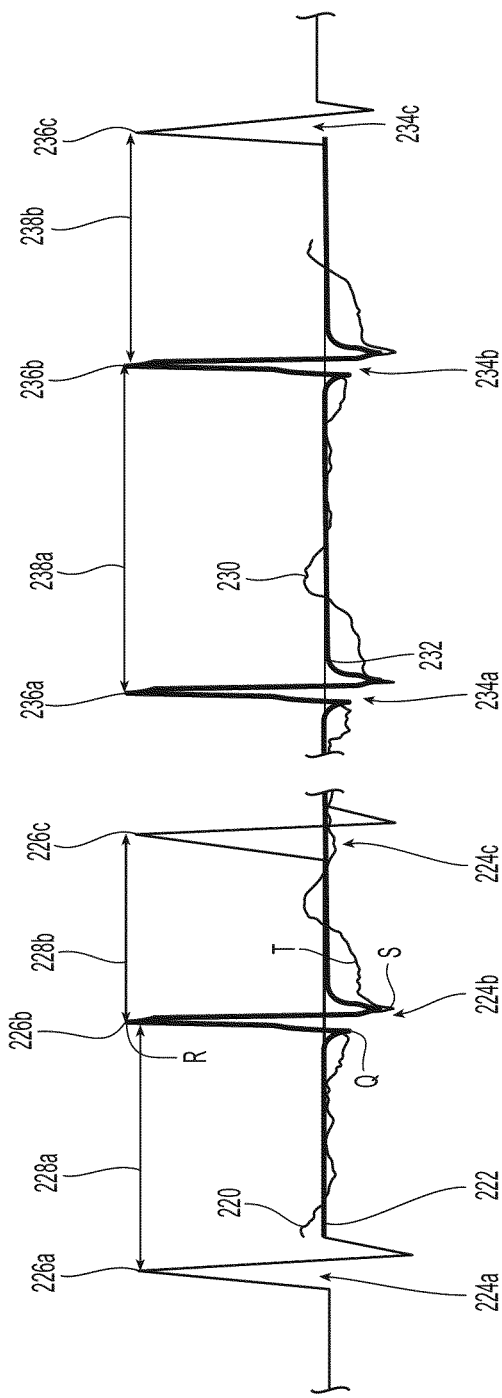
FIG. 11 is an illustrative view of an ECG waveform response in a subject patient to a vagus nerve stimulation treatment, according to an exemplary embodiment.

As shown in FIG. 5, in some embodiments, the computer processing device is programmed to provide for an R-R interval detector 70 and ECG processor 80. Embodiments of the R-R interval detector 70 and the ECG processor 80 are shown in FIGS. 9 and 10, respectively. The R-R interval detector 70 of FIG. 9 includes an ECG stimulation period identifier 72, a real-time QRS detector 74, a band pass filter 76, and an R-R interval verifier 78. The ECG stimulation period identifier 72 identifies portions of the incoming ECG response as corresponding to either the ON-period or the OFF-period of the stimulation signal to complete step 414 of FIG. 6. Illustrated in FIG. 11 is a first portion 220 of the sampled ECG-suitable signal corresponding to the ON-period of the stimulation signal and a second portion 230 of the sampled ECG-suitable signal corresponding to the OFF-period of the stimulation signal.

Each of the designated portions 220, 230 of the ECG waveform response is then processed to determine the components of the ECG waveform for further analysis and digital reconstruction. The real-time QRS detector 74 of the R-R interval detector 70 identifies the QRS-wave or complex, and the band pass filter 76 identifies the R-wave by detecting a maximum amplitude corresponding to the R-wave. Indicated in FIG. 11 are identified QRS complexes 224a, 224b, 224c for the ON-period ECG waveform portion 220 and the QRS complexes 234a, 234b, 234c of the OFF-period ECG waveform portion 230. Accordingly, each of the R-waves (226a, 226b, 226c) (236a, 236b, 236c) of the QRS complexes are also initially identified from baselines 222, 232.

The R-R interval (228a, 228b for the ON-period) (238a, 238b for the OFF-period), or time period between adjacent R-waves in the ECG waveform or equivalent ECG characterization, is then determined and verified by the R-R interval verifier 78 in real-time. The verifier 78 provides an interval timer or counter that determines the R-R interval and verifies that the R-R interval falls within a predetermined threshold value that corresponds to the periodic response of the incoming ECG-suitable signal. Accordingly, the R-R interval verifier 78 minimizes or eliminates mistakes in identification of the R-wave and R-R intervals. For example, the verifier 78 can filter out the amplitude of a T-wave from being mistaken for an R-wave by identifying the occurrence of the T-wave as being too close in time to the preceding R-wave. Thus, the R-R interval detector 70 completes the determination and filter steps 416, 418 in the process 400 of FIG. 6.

Figure 12:
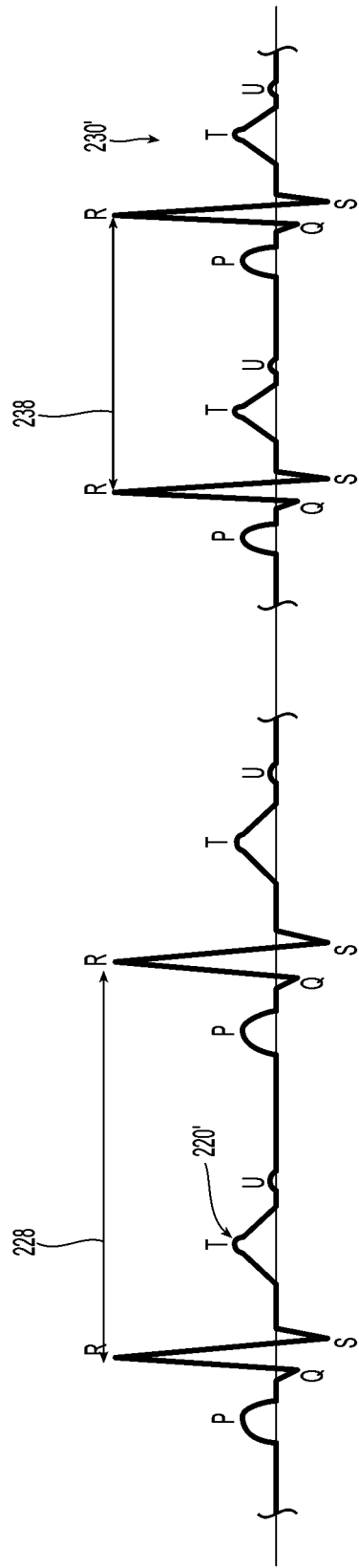
FIG. 12 is another illustrative view of an ECG waveform response in a subject patient to a vagus nerve stimulation treatment, according to an exemplary embodiment.

With each R-wave and R-R interval identified within the ECG waveform or equivalent, the computer processing device 50 determines one or more heart rate dynamics for assessment of the delivered stimulation signal. Referring again to FIG. 10, FIG. 10 illustrates an exemplary ECG processor 80 that includes one or more of a heart rate calculator 82, a heart rate variability calculator 84, and an ECG waveform generator 86. The heart rate calculator 82 determines an instantaneous heart rate ("IHR") between adjacent R-waves. Shown in FIG. 12 are adjacent R-waves in each of the ON-period portion 220' and the OFF-period 230' of the illustrative ECG waveform with respective determined R-R intervals (228, 238). Thus, in accordance with step 420 of the process 400 of FIG. 6, for each R-R interval, the IHR in beats per minute ("bpm") is determined by the following:

IHR=1 beat/(R-R interval msec)×(1000 msec/sec)× (60 sec/min)

From the IHR several statistical aspects of the heart rate can also be determined by the heart rate calculator 82. In some embodiments, the real-time heart rate can be determined at step 422 by taking a beat-to-beat average over a range of the latest recorded number of beats. For example, the real-time heart rate ("RTHR") can be determined by the average of the last five or fewer instantaneous heart rates. In some embodiments, the RTHR can be determined in step 422 of the process 400 by the average of the last three instantaneous heart rates in a manner as follows:

RTHR=[IHR(N)+IHR(N−1)+IHR(N−2)]/3, where N is the most recent IHR value, where N−1 is an IHR value preceding the N value in time, and where N−2 is an IHR value preceding the N value in time.

As can be appreciated, the IHR values can be qualified values that meet a threshold level of data quality, with inaccurate or inconsistent IHR values being disregarded, discounted, weighted, or modified to improve the quality of the IHR values used in the determination of the RTHR value. As can also be appreciated, the IHR(N), IHR(N−1), and IHR(N−2) values can be ordered in time in a sequence with each value being adjacent to the next in time, ordered in time in a sequence with unqualified IHR values interposed between qualified IHR values and/or ordered in time in a sequence with a skipped IHR value or values interposed between qualified IHR values. The RTHR may also be displayed (e.g., via the display 58) at step 422.

In a continuous manner, the storage memory 56b, in coordination with the R-R interval detector 70, stores in one or more data arrays each IHR, associated verified R-R interval, associated status identifier as either ON-period or OFF-period, and associated cycle number in the number of cycles defining the stimulus treatment. Accordingly, the heart rate calculator 82 determines, in real-time, the mean heart rate for each ON-period of stimulation signal delivery and OFF-period of rest in a given treatment cycle in steps 424, 426, respectively, of the process 400. For example, where a stimulation signal cycle is defined by a 14 second ON-period and a 66 second OFF-period, the heart rate calculator 82 takes the cumulative average of most or all the IHRs over the 14 second ON-period to determine the ON-period mean heart rate ("(MHR)ON"). To determine the OFF-period mean heart rate ("(MHR)OFF"), the heart rate calculator 82 takes the cumulative average of most or all IHRs over the 66 second OFF-period. In one embodiment, the IHR values corresponding to the ON-period and/or the OFF-period can be qualified to eliminate low-quality IHR values or to eliminate IHR values that overlap or are proximate to the start or cessation of stimulation.

Additionally or alternatively to taking the cumulative average of all determined instantaneous heart rates to calculate mean heart rates, the heart rate calculator 82 can apply a data quality process that prefers, uses, or takes the cumulative average of the instantaneous heart rates within 25% of the mean of instantaneous heart rates for a given ON-period or OFF-period. Thus, the heart rate calculator 82 eliminates extremes in instantaneous heart rates in each of the ON-period and OFF-period by defining the minimum instantaneous heart rate at 25% below the mean and defining the maximum instantaneous heart rate at 25% above the mean. The heart rate calculator 82 can then determine the mean heart rate ("MHR") by taking the cumulative average of instantaneous heart rates falling between the maximum and minimums. The mean heart rate may also be displayed for the ON-period and OFF-period at steps 424, 426, respectively.

In step 428 of process 400, the heart rate calculator 82 determines (e.g., in real-time) the extent of bradycardia response. For example, the heart rate calculator 82 determines a heart rate reduction response for each cycle of treatment by determining the difference between the cumulative averages of the instantaneous heart rates to indicate a heart rate reduction ("HRR") as follows:

HRR=(MHR)OFF−(MHR)ON

A positive HRR indicates a bradycardia response, and a negative HRR indicates a tachycardia response. A positive HRR reduction of less than 5% from the mean heart rate for the OFF-period ((MHR)OFF) indicates a desired response of autonomic engagement (e.g., a response within the neural fulcrum zone). The HRR may also be displayed at step 428.

Figure 13:
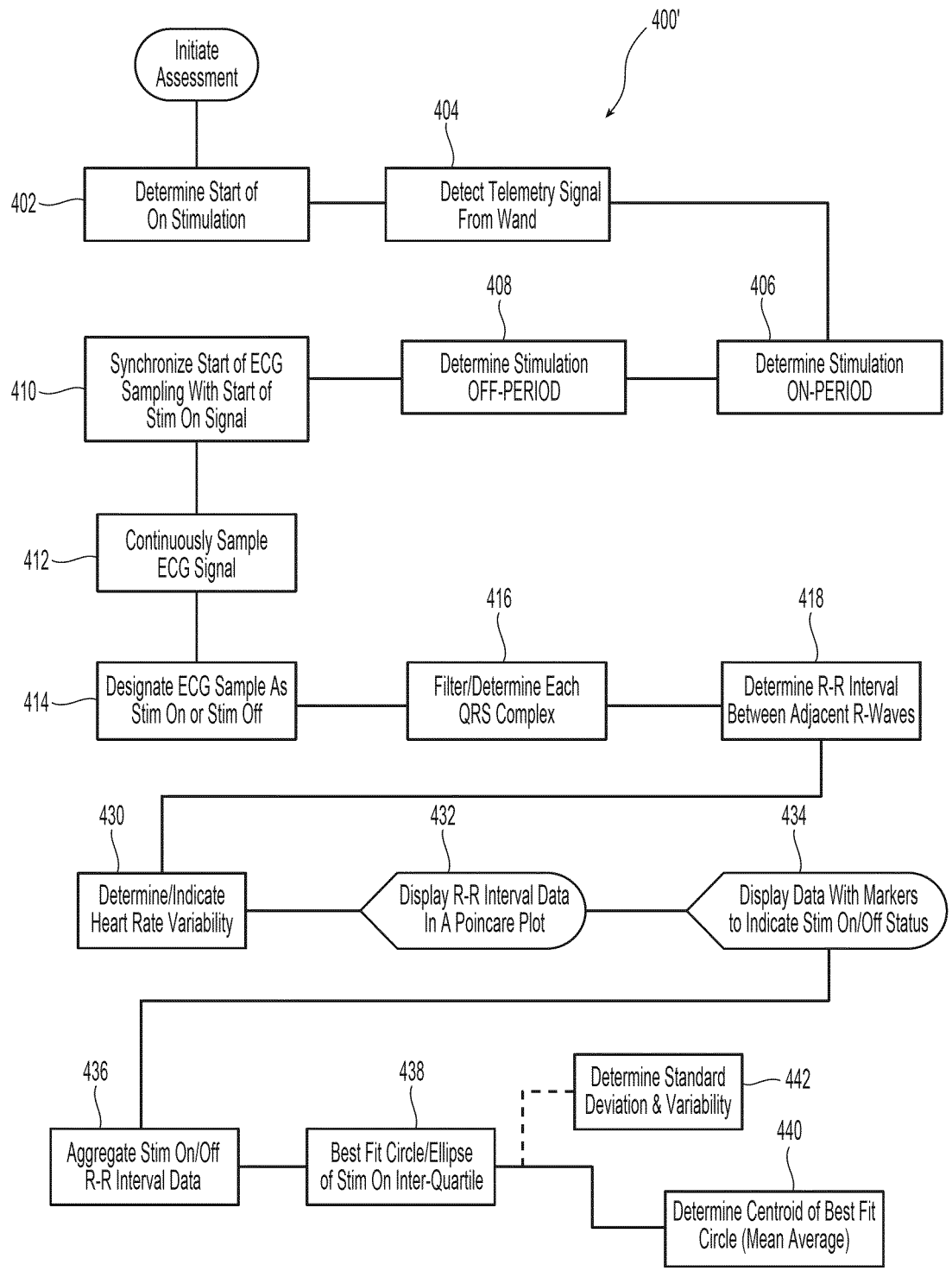
FIG. 13 is another embodiment of a method for assessing autonomic engagement response to vagus nerve stimulation therapy using the system of FIG. 2.

Referring again to FIG. 10, the ECG processor 80 includes a heart rate variability calculator 84 to determine heart rate variability in step 430 of an additional or alternate method 400' for assessing response to the vagus nerve stimulation as shown in FIG. 13. In particular, the variability calculator 84 determines a difference in the heart rate variability response between the ON-period and the OFF-period. In an aspect, the storage memory 56b, in coordination with the ECG processor 80 and variability calculator 84, stores in one or more data arrays the R-R interval for each preceding R-R interval and stimulation status ON/OFF period for a number of cycles in the stimulation treatment. Accordingly, the stored data array can be defined as {R-R Interval(N+1), R-R Interval(N), ON/OFF-period Status, #Cycle}. The data can be aggregated for each cycle in a manner that differentiates ON-period of stimulation signal delivery and OFF-period of resting period. In some embodiments, for each cycle, the mean average of all the R-R Intervals for the ON-period and the mean average of all the R-R Intervals for the OFF-period are determined and compared. A separation in the mean average can be used to show an autonomic engagement response to the delivery of vagus nerve stimulation treatment.

Figure 14:
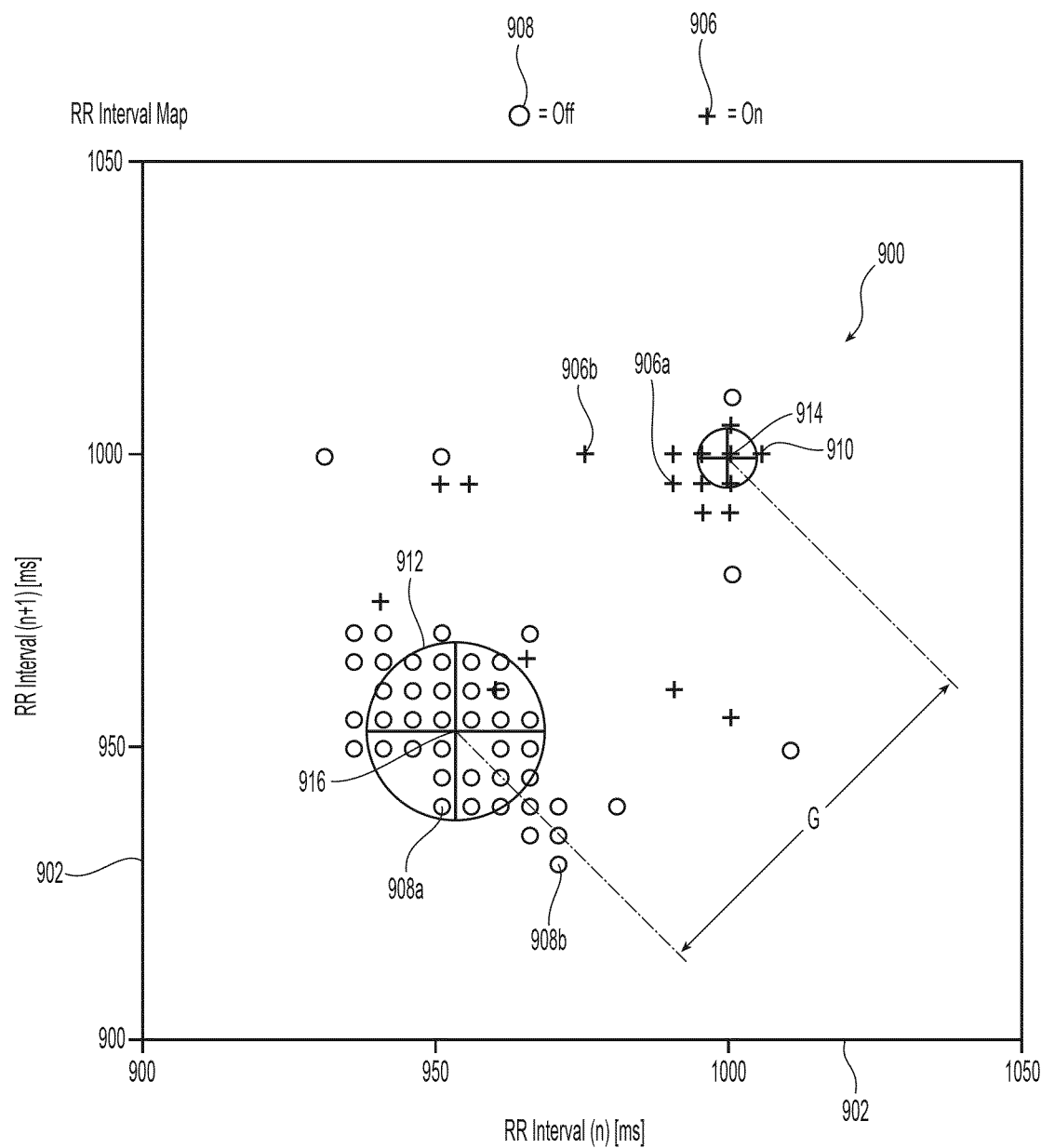
FIG. 14 is an illustrative view of a Poincare plot display generated from the method of FIG. 13, according to an exemplary embodiment.
Figure 15:
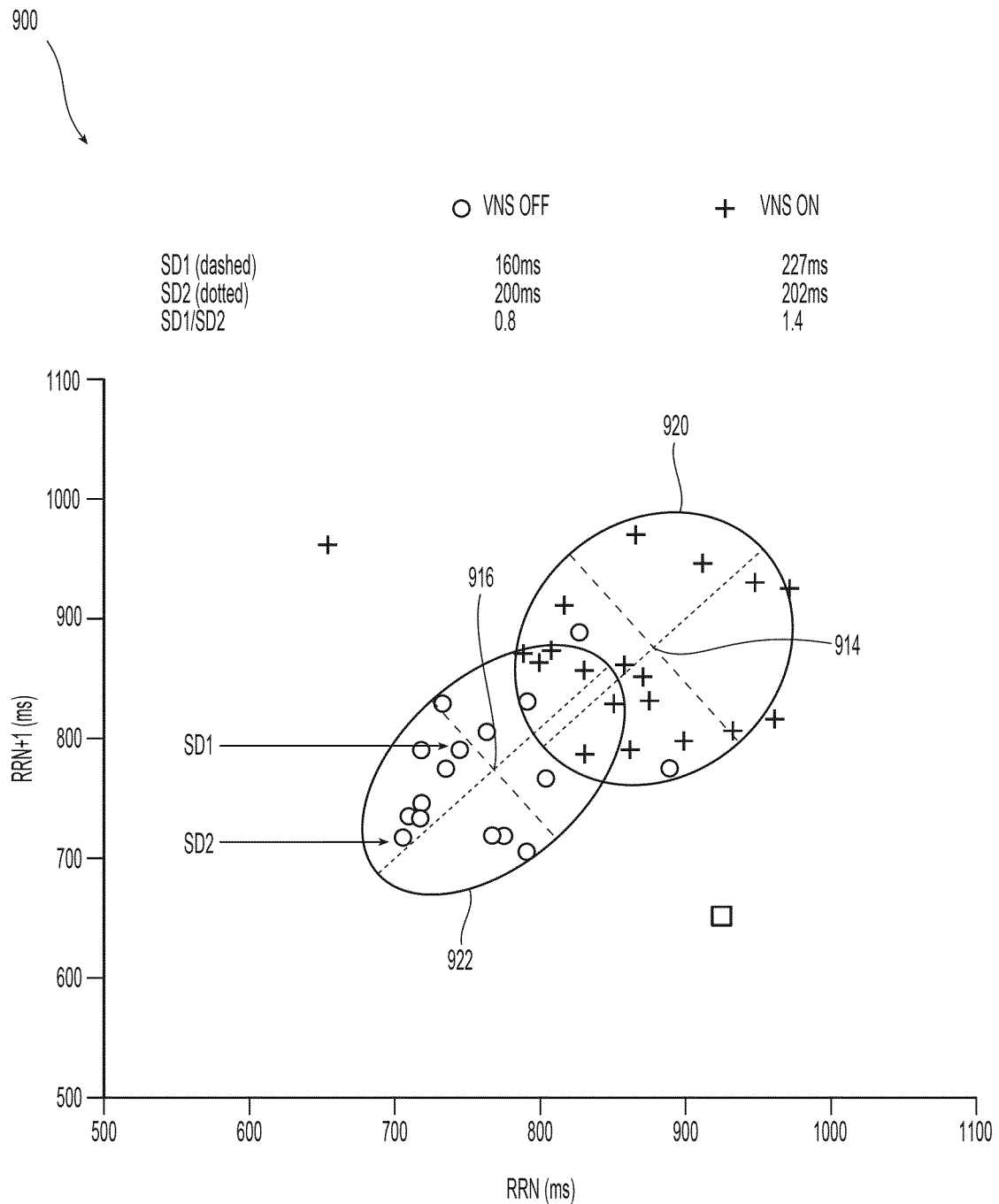
FIG. 15 is an illustrative view of another Poincare plot display generated from the method of FIG. 13, according to an exemplary embodiment.

In an aspect of the assessment method 400', the heart variability is graphically displayed in a display step 432 that provides the subject patient SP or clinician with a real-time indicator of autonomic engagement response to a delivered stimulus. More particularly, the R-R interval differential between the ON-period and OFF-period is displayed in a Poincaré plot 900 as illustrated in FIG. 14 and FIG. 15. The display can be generated (e.g., in real-time) for the subject patient SP or clinician to view at the display 58 of the system 10. The plot shows the R-R interval (R-R Interval(N+1)) along the vertical axis 902 in msec, as a function of the preceding R-R interval (R-R Interval(N)) along the horizontal axis 904 in msec. In step 434 of the process 400', the R-R intervals for the ON-period and OFF-period are distinguished from one another by differentiating markers, as shown in FIGS. 14 and 15. R-R interval values for the ON-period are shown with "+" markers 906, and the OFF-period values are shown with "O" markers 908. In accordance with an aggregating step 436 of the process 400', the plot 900 provides a visual indication of autonomic engagement as determined by the separation or gap G between the cluster of ON-period R-R interval values from the cluster of OFF-period R-R interval values.

In another process step 438, the plot 900 shows a first best-fit circle 910 about the R-R interval ON-period data (e.g., 906a, 906b) and a second best-fit circle 912 about the R-R interval OFF-period data (e.g., 908a. 908b). The best-fit circles 910, 912 are defined by a radius about the centroids 914, 916, which are determined by the respective means of the ON-period and OFF-period R-R interval data at step 440. The radii of the best-fit circles 910, 912 are calculated or defined by a minimum and maximum in the R-R interval values about the mean. In some embodiments, the heart rate variability calculator 84 determines the 25th quartile and the 75th quartile of the R-R interval values and determines the mean of values falling between the 25th and the 75th quartiles about which to determine the best fit circles. The gap G is defined as the straight line distance between the centroids 914, 916 to indicate an extent of autonomic engagement. Alternatively, the heart rate variability calculator 84 defines the minimum R-R interval value at 25% below the mean and defines the maximum R-R interval value at 25% above the mean. In another alternative, the best-fit circles 910, 912 include or circumscribe each of the minimum and maximum values.

Shown in FIG. 15, are additional graphical indicators in a plot 900' indicating heart rate variability response to the vagus nerve stimulation treatment. The heart rate variability calculator 84 can determine and aggregate, as alternatively provided in step 438 of the process 400' of FIG. 13, the R-R interval data to best-fit ellipses 920, 922 for each of the ON-period and OFF-period data to indicate the extent of heart rate variability within each respective period during stimulation delivery and during the resting period. The calculator 84 can determine each of the major axis SD2 and the minor axis SD1 for each of the ellipses 920, 922 as part of determining standard deviation and variability at step 442 of the process 400'. In some embodiments, the minor axis SD1 is determined as reflecting the standard deviation of the IHR about the mean, and the major axis SD2 is determined as the standard deviation of the continuous heart rate about the mean. The major axis SD2 can be found by a best fit to the data with the axis SD2 passing through the centroid or mean 914, 916 of the R-R interval. The minor axis SD1 extends transverse to the major axis SD2 and passes through the centroid 914, 916. Accordingly, the ellipse 920, 922 is a best fit that is centered about the centroid 914, 916, respectively, and passes through the axes SD2, SD1 while encompassing the data disposed about the respective centroid 914, 916.

Figure 16:
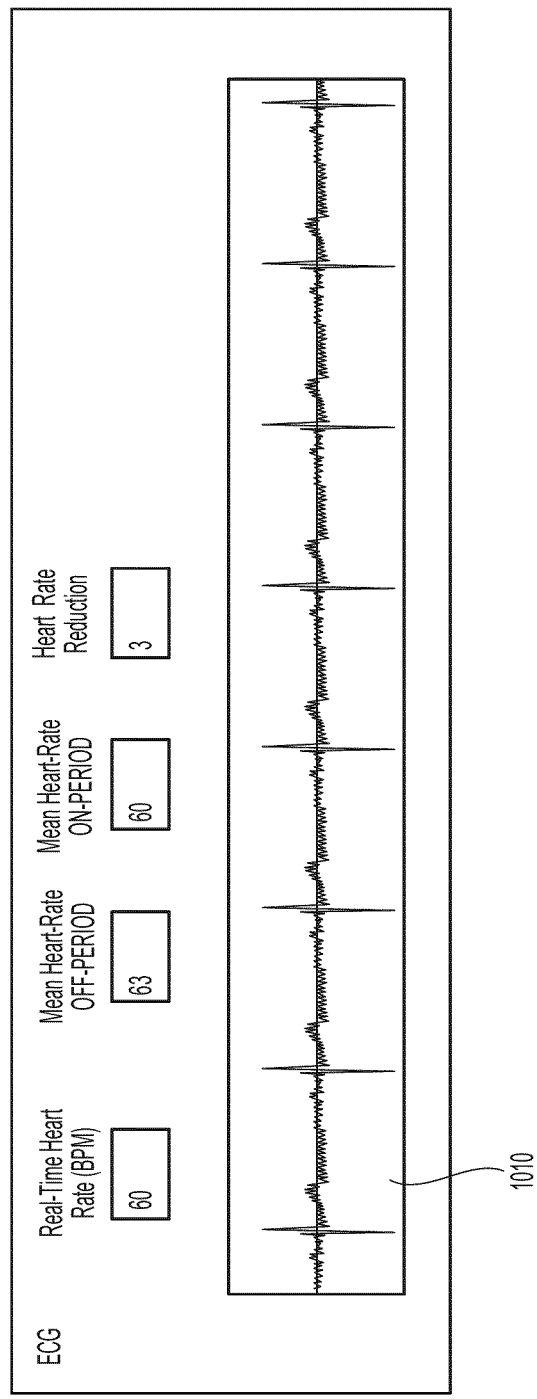
FIG. 16 is an illustrative view of a digital replica of an ECG waveform response and various heart rate dynamics generated from the method of FIG. 6, according to an exemplary embodiment.

Given the data compiled and collected by the computer processing device 50, the ECG processor 80 can also include an ECG waveform generator 86, as seen in FIG. 10. At step 450 of method 400, the waveform generator 86 can display a digital replica of the ECG waveform 1010 in the display 58 in real-time, as shown, for example, in FIG. 16. The ECG replica 1010 includes all the PQRSTU intervals of the waveform to provide a visual indicator to the subject patient, clinician, and/or physician of any possible arrhythmia to accompany the assessment indicators previously described. Moreover, the display 58 can display back to the subject patient or clinician each of the determined values from the assessment processes previously described. For example, the display 58 can report back the real-time heart rate (RTHR), the mean heart rates for each of the OFF-Period and ON-Period ((MHR)OFF, (MHR)ON), and the Heart Rate Reduction (HRR). Additionally, in some embodiments, the display 58 can show the R-wave axis and/or mark the R-wave intervals for the subject patient or clinician.

For the purpose of this disclosure, the term "coupled" means the joining of two members directly or indirectly to one another. Such joining may be achieved with the two members or the two members and any additional intermediate members being integrally formed as a single unitary body with one another, or with the two members or the two members and any additional intermediate members being attached to one another. Such joining may be permanent in nature or may be removable or releasable in nature.

While the present disclosure makes reference to certain embodiments, numerous modifications, alterations, and changes to the described embodiments are possible without departing from the sphere and scope of the present disclosure, as defined in the appended claims. Accordingly, it is intended that the present disclosure not be limited to the described embodiments, but that it has the full scope defined by the language of the following claims and equivalents thereof

What is claimed is:

1. An assessment system for vagus nerve stimulation therapy treatment for congestive heart failure in a subject implanted with a neurostimulator configured to deliver a periodic stimulation signal having a plurality of ON-periods and OFF-periods, each ON-period being defined as a time between an initiating pulse and a terminating pulse of a plurality of stimulation pulses delivered to the subject, each OFF-period being defined as a time between consecutive ON-periods, the assessment system comprising:

a wand assembly in communication with the neurostimulator, the wand assembly configured to detect a delivery of the periodic stimulation signal from the neurostimulator to the subject and to generate a delivery detection signal indicating the detected delivery of the periodic stimulation signal;

a lead assembly configured to acquire an ECG signal of the subject over the plurality of ON-periods and OFF-periods;

a data acquisition system coupled to the wand and lead assemblies and configured to capture each of the delivery detection signal and the ECG signal; and a processor and a non-transitory computer-readable memory storing instructions that, when executed by the processor, cause the assessment system to:

record the ECG signal over at least one successive pair of ON- and OFF-periods including, for each pair of ON- and OFF-periods, synchronizing a start of the recorded ECG signal using the delivery detection signal to provide a first portion of the recorded ECG signal corresponding to the ON-period and a second portion of the recorded ECG signal corresponding to the OFF-period;

determine a heart rate dynamic response from the ECG signal, including:

detecting each QRS complex in each of the first and second portions of the recorded ECG signal;

identifying each potential R-wave in each QRS complex in each of the first and second portions of the recorded ECG signal;

verifying each identified R-wave in each of the first and second portions of the recorded ECG signal; and determining an R-R interval between each pair of successive verified R-waves;

determine an instantaneous heart rate for each determined R-R interval to determine heart rate dynamics for assessment of autonomic engagement in response to the vagus nerve stimulation therapy treatment; and display the recorded ECG signal in real-time.

2. The system of claim 1, wherein the instructions further cause the assessment system to differentiate between the first and second portions of the ECG signal and display the instantaneous heart rates for at least one ON-period and for at least one OFF-period.

3. The system of claim 1, wherein the instructions further cause the assessment system to differentiate between the first and second portions of the ECG signal and display a cumulative average of the instantaneous heart rates for at least one ON-period and a cumulative average of the instantaneous heart rates for at least one OFF-period.

4. The system of claim 1, wherein the instructions further cause the assessment system to determine heart rate reduction as a difference between a cumulative average of the instantaneous heart rates for at least one ON- period and a cumulative average of the instantaneous heart rates for at least one OFF-period.

5. The system of claim 1, wherein the instructions cause the assessment system to record the ECG signal continuously for a plurality of successive pairs of ON- and OFF-periods.

6. The system of claim 1, wherein the instructions cause the assessment system to determine a real-time heart rate by averaging instantaneous heart rates of the last three R-R intervals.

7. The system of claim 1, wherein the instructions cause the assessment system to determine heart rate variability from each determined R-R interval in each of the first and second portions of the recorded ECG signal.

8. The system of claim 7, wherein the instructions cause the assessment system to differentiate between the first and second portions of the ECG signal and display the heart rate variability for at least one ON-period and for at least one OFF-period.

9. The system of claim 8, wherein the instructions cause the assessment system to determine the heart rate variability from each determined R-R interval within 25% of a mean R-R interval for each of the first and second portions of the recorded ECG signal.

10. The system of claim 1, wherein the data acquisition system is configured to sample the ECG signal at a rate of at least 200 samples per second.

11. The system of claim 1, wherein the stimulation signal ramps up at a constant rate from the OFF-period to the initiating pulse for each successive pair of ON- and OFF-periods.

12. The system of claim 1, wherein the stimulation signal ramps down at a constant rate from the terminating pulse to the OFF-period for each successive pair of ON- and OFF-periods.

13. An assessment system for vagus nerve stimulation therapy treatment for congestive heart failure in a subject, the assessment system comprising:

a wand assembly in communication with a neurostimulator, the wand assembly configured to detect a delivery of a periodic stimulation signal of vagus nerve stimulation delivered to the subject from the neurostimulator and to generate a delivery detection signal indicating the detected delivery of the periodic stimulation signal;

a lead assembly configured to acquire an analog ECG signal of the subject over a delivery period of the periodic stimulation signal of the vagus nerve stimulation delivered to the subject and defined by an initiating pulse and a terminating pulse, the delivery period being a time between the initiating and terminating pulses;

a data acquisition system coupled to the wand and lead assemblies and configured to convert the analog ECG signal to a digital ECG signal over the delivery period; and a processor and a non-transitory computer-readable memory storing instructions that, when executed by the processor, cause the assessment system to:

synchronize a start of the digital ECG signal to the delivery period using based on the delivery detection signal;

detect each QRS complex in the digital ECG signal over the delivery period;

identify each potential R-wave in each QRS complex of the digital ECG signal;

confirm each R-wave of the digital ECG signal;

determine a time interval between each pair of successive confirmed R-waves of the digital ECG signal;

determine an instantaneous heart rate from each determined time interval; and determine a cumulative average of the instantaneous heart rates during the delivery period.

14. The system of claim 13, wherein the digital ECG signal of the delivery period is a first ECG signal;

wherein the lead assembly is configured to acquire an analog ECG signal of the subject over a resting period, the resting period being a time after the terminating pulse in which no stimulation is delivered to the subject, and wherein the data acquisition system is configured to convert the analog ECG signal over the resting period to a second ECG signal being a digital ECG signal of the resting period; and wherein the instructions further cause the assessment system to determine a time interval between each pair of successive confirmed R-waves of the second ECG signal and determine an instantaneous heart rate from each determined time interval of the second ECG signal.

15. The system of claim 14, wherein the instructions further cause the assessment system to determine a cumulative average of the instantaneous heart rates during the resting period and determine a difference between the cumulative averages of the instantaneous heart rates to indicate a heart rate reduction.

16. The system of claim 15, wherein the instructions further cause the assessment system to plot a Poincaré plot comprising the time interval between each pair of successive R-waves plotted against the time interval between each pair of immediately subsequent successive R-waves for the first ECG signal and the second ECG signal.

17. The system of claim 13, wherein the instructions further cause the assessment system to determine a real-time heart rate by averaging the last three instantaneous heart rates.

18. The system of claim 13, wherein the instructions further cause the assessment system to:
determine R-R intervals of an ON-period portion of the digital ECG signal and R-R intervals of an OFF-period portion of the digital ECG signal to determine heart rate variability of each of the ON-period portion and the OFF-period portion; and
display the heart rate variabilities.

19. The system of claim 13, further comprising the neurostimulator, wherein the neurostimulator is an implantable medical device configured to generate the vagus nerve stimulation.

20. The system of claim 19, wherein the implantable medical device includes an implantable cardioverter-defibrillator (ICD).

21. A method of real-time assessment of autonomic engagement response to vagus nerve stimulation therapy, the method comprising:
receiving a delivery detection signal from a wand assembly in communication with a neurostimulator, the delivery detection signal indicating a delivery of a periodic stimulation signal of the vagus nerve stimulation therapy delivered to a subject from the neurostimulator detected by the wand assembly;
determining, in real-time, R-R intervals in an ECG signal response to a stimulation cycle of the vagus nerve stimulation therapy, the stimulation cycle having an ON-period during which therapy is delivered and an OFF-period during which therapy is not delivered; and
distinguishing the R-R intervals occurring during the ON-period from the R-R intervals occurring during the OFF-period using the delivery detection signal to assess the autonomic engagement response to the stimulation cycle.

22. The method of claim 21, further comprising recording an ECG signal over at least one successive pair of ON- and OFF-periods, synchronizing a start of the recorded ECG signal to provide a first portion of the recorded ECG signal corresponding to the ON-period and a second portion of the recorded ECG signal corresponding to the OFF-period.

23. The method of claim 22, further comprising determining heart rate variability from each determined R-R interval in each of the first and second portions of the recorded ECG signal.

24. The method of claim 23, further comprising displaying the heart rate variability for at least one ON-period and for at least one OFF-period.

25. The method of claim 21, further comprising determining an instantaneous heart rate for each determined R-R interval to determine heart rate dynamics to assess the autonomic engagement response to the stimulation cycle.

26. The method of claim 21, further comprising displaying instantaneous heart rates for at least one ON-period and for at least one OFF-period.

27. The method of claim 21, further comprising displaying a cumulative average of instantaneous heart rates for at least one ON-period and a cumulative average of instantaneous heart rates for at least one OFF-period.

28. The method of claim 21, further comprising determining a heart rate reduction as a difference between a cumulative average of instantaneous heart rates for at least one ON-period and a cumulative average of instantaneous heart rates for at least one OFF-period.

29. The method of claim 21, further comprising determining a real-time heart rate by averaging instantaneous heart rates of the last three R-R intervals.

* * * * *